United States Patent [19]
Shiber

[11] Patent Number: 5,306,244
[45] Date of Patent: Apr. 26, 1994

[54] METHOD OF GUIDEWIRE INSERTION

[75] Inventor: Samuel Shiber, Billerica, Mass.

[73] Assignee: Surgical Systems & Instruments, Inc., Ill.

[21] Appl. No.: 662,558

[22] Filed: Feb. 28, 1991

Related U.S. Application Data

[63] Continuation-in-part of Ser. No. 499,726, Mar. 27, 1990, Pat. No. 5,135,531, which is a continuation-in-part of Ser. No. 350,020, May 12, 1989, Pat. No. 4,979,939, which is a continuation-in-part of Ser. No. 326,967, Mar. 22, 1989, Pat. No. 4,957,482, Ser. No. 324,616, Mar. 16, 1989, Pat. No. 5,007,896, Ser. No. 323,328, Mar. 13, 1989, Pat. No. 5,002,553, and Ser. No. 322,497, Mar. 13, 1989, Pat. No. 5,024,651, said Ser. No. 326,967, said Ser. No. 324,616, said Ser. No. 323,328, said Ser. No. 322,497, is a continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 78,042, Jul. 27, 1987, Pat. No. 4,819,634, Ser. No. 205,479, Jun. 13, 1988, Pat. No. 4,883,458, and Ser. No. 225,880, Jul. 29, 1988, Pat. No. 4,842,579, said Ser. No. 78,042, said Ser. No. 205,479, said Ser. No. 225,880, is a continuation-in-part of Ser. No. 18,083, Feb. 24, 1987, Pat. No. 5,041,082, which is a continuation-in-part of Ser. No. 874,546, May 16, 1986, Pat. No. 4,732,154, which is a continuation-in-part of Ser. No. 609,846, May 14, 1984, abandoned.

[51] Int. Cl.$^5$ ............................................. A61B 17/32
[52] U.S. Cl. ............................ 604/53; 606/159; 606/170; 128/772
[58] Field of Search ............... 604/22, 96, 265, 53; 606/159, 170, 171, 180, 194; 128/30, 202.12, 772, 897

[56] References Cited

U.S. PATENT DOCUMENTS

| | | | |
|---|---|---|---|
| 826,029 | 7/1906 | Harper | 128/202.12 |
| 2,506,865 | 5/1950 | Forrey | 128/30 |
| 3,903,869 | 9/1975 | Bancalari | 128/202.12 |
| 4,445,509 | 5/1984 | Auth | 606/159 |
| 4,471,688 | 9/1984 | Smets | 128/897 |
| 4,589,412 | 5/1986 | Kensey | 606/159 |
| 4,631,052 | 12/1986 | Kensey | 604/22 |
| 4,669,469 | 6/1987 | Gifford, III et al. | 606/159 |
| 4,685,458 | 8/1987 | Leckrone | 606/159 |
| 4,696,667 | 9/1987 | Masch | 604/22 |
| 4,732,154 | 3/1988 | Shiber | 606/159 |
| 4,883,458 | 11/1989 | Shiber | 606/159 |
| 4,898,575 | 2/1990 | Fischell et al. | 604/22 |
| 5,087,244 | 2/1992 | Wolinsky et al. | 606/194 |
| 5,098,381 | 3/1992 | Schneider | 604/96 |
| 5,102,402 | 4/1992 | Dror et al. | 604/265 |
| 5,127,902 | 7/1992 | Fischell | 606/159 |

OTHER PUBLICATIONS

*Factors Influencing Restonosis after Coronary Angioplasty*, Pompa and Topol, Am. J. of Medicine, Jan. 1990.
Waller et al., *Morphologic Observations Late After Coronary Balloon Angioplasty*, Radiology, Mar. 1990.
Arrow International, Inc., Reading, PA 19610, "CPAC System" Nov. 1990.

*Primary Examiner*—Ralph Lewis
*Attorney, Agent, or Firm*—Samuel Shiber

[57] ABSTRACT

An atherectomy system for coring, ingesting and removing plaque from within a patient's vessel having a flexible guide wire defining a void for holding plaque during the atherectomy process and for accurately guiding a flexible catheter in the vessel. Coupling means at the proximal end of the flexible catheter for coupling it to drive means. The insertion of the guidewire may be assisted by suspending a body part in a decompression chamber to dilate the vessel.

1 Claim, 5 Drawing Sheets

METHOD OF GUIDEWIRE INSERTION

CROSS REFERENCE TO OTHER APPLICATIONS

This application is a continuation-in-part (CIP) of application Ser. No. 07/499,726 filed Mar. 27, 1990 (now U.S. Pat. No. 5,135,531) which is a continuation-in-part of application Ser. No. 07/350,020 filed May 12, 1989 (now U.S. Pat. No. 4,979,939) which is a continuation-in-part of four applications: application Ser. No. 07/326,967 filed Mar. 22, 1989 (now U.S. Pat. No. 4,957,482), application Ser. No. 07/324,616 filed Mar. 16, 1989 (now U.S. Pat. No. 5,007,896), application Ser. No. 07/323,328 filed Mar. 13, 1989 (now U.S. Pat. 5,002,553), and application Ser. No. 07/322,497 filed Mar. 13, 1989 (now U.S. Pat. No. 5,024,651). These four applications are continuation-in-parts of application Ser. No. 07/286,509 filed Dec. 19, 1988 (now U.S. Pat. No. 4,894,051) which is a continuation-in-part of application Ser. No. 07/243,900 filed Sep. 13, 1988 (now U.S. Pat. No. 4,886,490), which is a continuation-in-part of three applications, application Ser. No. 07/078,042 filed Jul. 27, 1987 (now U.S. Pat. No. 4,819,634), application Ser. No. 07/205,479 filed Jun. 13, 1988 (now U.S. Pat. No. 4,883,458), and application Ser. No. 07/225,880 filed Jul. 29, 1988 (now U.S. Pat. No. 4,842,579). These three applications are continuation-in-parts of application Ser. No. 07/018,083 filed Feb. 24, 1987 (now U.S. Pat. No. 5,041,082), which is a continuation-in-part of application Ser. No. 06/874,546 filed Jun. 16, 1986 (now U.S. Pat. No. 4,732,154) which is a continuation-in-part of application Ser. No. 06/609,846 filed May 14, 1984 (abandoned).

All the above applications are being incorporated herein by reference.

BACKGROUND AND OBJECTIVES OF THE INVENTION

With age a large percentage of the population develops atherosclerotic arterial obstructions causing a diminished blood circulation and blood clots 7hich further diminish or block the blood flow. When this process occurs in a coronary artery it is referred to as a heart attack. Commonly such conditions are treated surgically by grafting a bypass, or by less invasive procedures such as angioplasty or atherectomy. These less invasive procedures are less traumatic to the patient, are usually performed under local anesthesia, a brief hospitalization is usually sufficient and their direct and indirect costs are a fraction as compared to by-pass surgery. A major shortcoming of angioplasty is a high rate of re-closure of the artery or "restenosis". Angioplasty does not remove the obstruction but instead it radially displaces the atherosclerotic plaque and often tears the arterial wall. This triggers excessive proliferation of smooth muscle cell in the medial arterial layer (hyperplasia) and blood clotting, which are the major causes of restenosis of the newly created lumen (neolumen). Additionally elastic recoil of the arterial wall partially negates the effect of angioplasty.

An objective of the present invention minimizes restenosis by: A) Extracting the plaque, thereby minimize the elastic recoil B) Forming a smooth continuous lumen, thereby minimizing blood clotting C) Minimizing injury to the arterial wall, thereby minimizing hyperplasia D) Applying restenosis inhibiting drugs to the atherectomy site which inhibit blood clotting and hyperplasia proliferation. Drugs which are currently accepted, or being evaluated, for such purpose are, for example: 1) Hirudin, which blocks thrombin-platelet receptors preventing platelet aggregation and subsequent release of platelet derived growth factor (PDGF) which stimulates hyperplasia 2) Low-molecular weight heparin, the non-anticoagulant fragment of heparin believed to directly alter the smooth muscle cells' life cycle 3) Glucocorticoids, which are steroids believed to inhibit the production of PDGF-like material by smooth muscle cells and the radial migration of smooth muscle cells through the arterial wall 4) Angiopeptin, a peptitde analogue of Somatostatin believed to inhibit smooth muscle cell production of a hyperplasia causing growth factor 5) Angiotensin converting enzyme inhibitor, which is believed to inhibit hyperplasia 6) Antimitogenics, which directly inhibit hyperplasia 7) Antiplatelets antibodies, which reduce the release of PDGF 8) Endotilin neutralizer which inhibits the vasoconstriction and cell proliferation caused by Endotilin which is secreted by injured endothal cells. It can be appreciated that there is on-going research in this area which periodically suggests that additional drugs would fit this category of restenosis inhibiting drugs, and such drugs may also be applied to the atherectomy site by this system. Additional information on such research may be found in the abstracts published by the Division of Cardiology, Department of Internal Medicine, of the University of Michigan in Ann Arbor covering a conference held in May 17-18, 1990 Titled the Restenosis Summit II.

Another objective is to provide a system that can be made in large and small diameters, down to approximately 1 mm (millimeter) and a length of approximately a meter, to reach and enter small and remote arteries. A further objective is to utilize the physician's existing skills accessing the artery and placing a guide wire through the obstruction.

The above and other objectives of the invention will become apparent from the following discussion and the accompanying drawings.

BRIEF DESCRIPTION OF THE FIGURES

FIG. 5' shows two optional blade configurations.

DETAILED DESCRIPTION OF THE DRAWINGS

Figures 1, 3, 4, 5, 6:
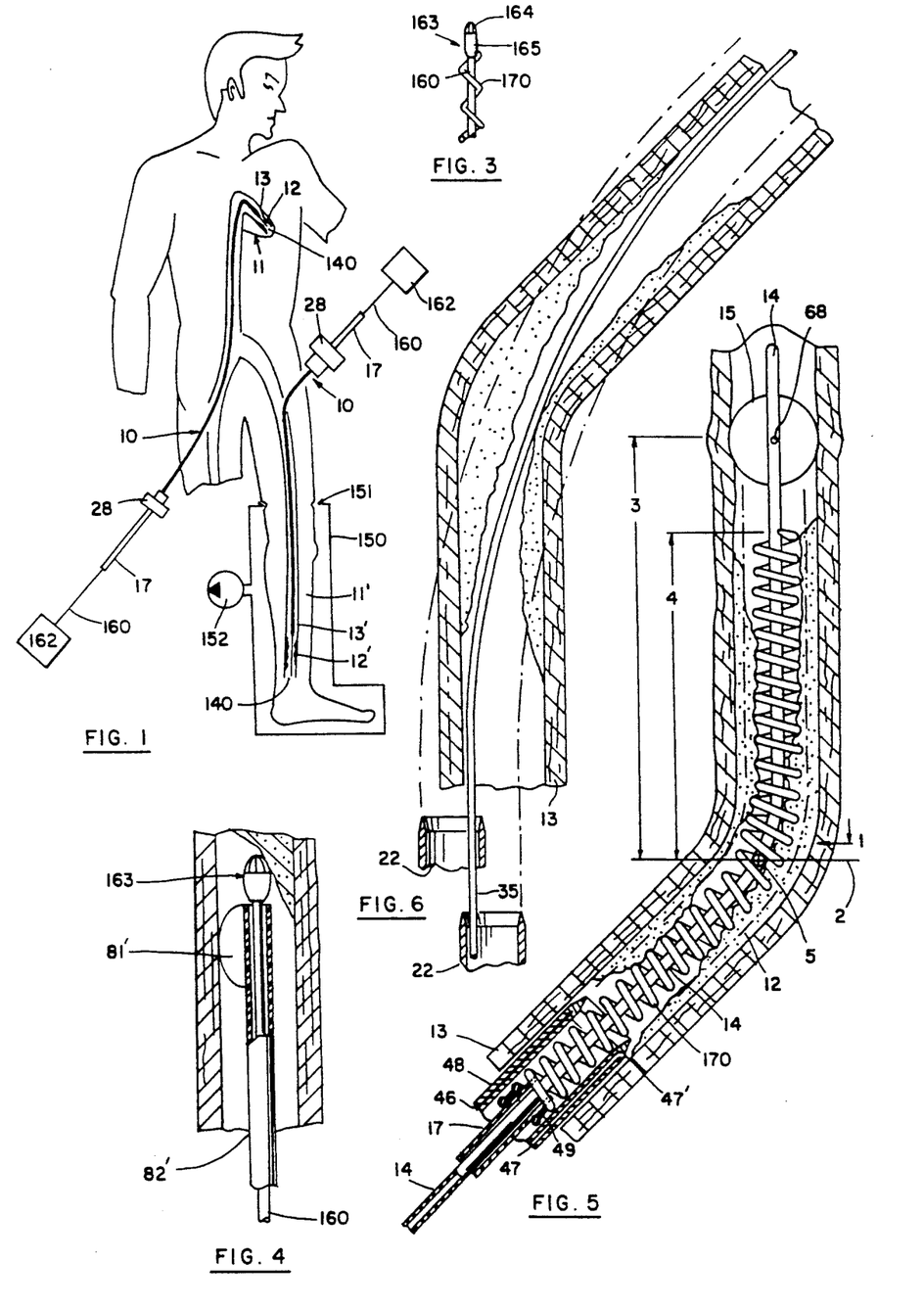
FIG. 1 generally shows an atherectomy system inserted at the groin area, through the skin, through a patient's arterial system, into a coronary vessel serving the patient's heart. A second atherectomy system is inserted at the groin area, through the skin, into a vessel of a leg which is disposed in a de-compression chamber.
FIG. 3 shows a distal end portion of a flexible guide wire with an ultrasound pod having teeth on its distal end.
FIG. 4 shows a distal end portion of a flexible pilot wire with a similar pod to the one shown in FIG. 3, disposed in a deflecting sleeve.
FIG. 5 shows the trajectory of the system in a cross sectioned, curved obstructed artery, when the coring process is done over a flexible guide wire having a casing over which the flexible catheter is accurately guided.
FIG. 6 shows the possible range of trajectories of the system in a cross sectioned, curved obstructed artery, when the coring process is done over a standard flexible guide wire without a casing.

FIG. 1 generally shows one atherectomy system 10 inserted at the groin area through the skin, through a patient's arterial system, into a coronary vessel 13 serving the patient's heart 11. A second atherectomy system 10 (similar parts will be indicated by the same numbers throughout the FIGS.) is inserted at the groin area through the skin, into a vessel 13' serving the lower leg 11' containing an obstruction 12'. The leg is suspended in a de-compression chamber 150 having an opening 151 which seals around the leg and allows a pump 152 to regulate the pressure within the chamber 150. Lowering the pressure surrounding the leg and suspending it in a negative pressure dilates the vessel 13' and thereby eases the insertion of the guidewire into the vessel prior to the atherectomy procedure and eases extraction of the system after the procedure. Since suction is limited to 1 atmosphere of pressure, it is possible to apply positive pressure during the atherectomy procedure (for example by reversing the pump 152), and then apply negative pressure after the procedure, thereby increasing the pressure drop and further easing the extraction of the system.

Figure 2:
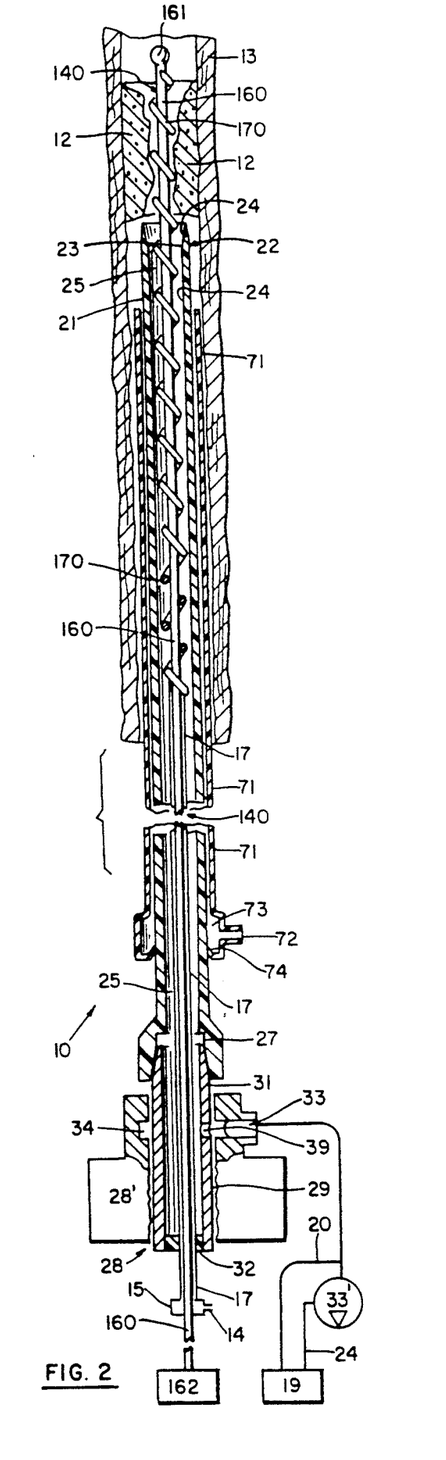
FIG. 2 shows a cross sectioned view of an atherectomy system with a flexible guide wire made of a flexible casing in the form of a helical wire attached to a proximal extension tube and a flexible pilot wire incorporating an ultrasound pod. The middle portion of the atherectomy system is removed due to space limitations on the drawing sheet.
Figure 5:
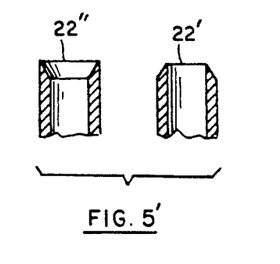

FIG. 2 shows the atherectomy system 10 for removing an obstruction 12 from within the patient's vessel 13 and applying a drug to the atherectomy site. The atherectomy system comprises several elongated parts in a nested relationship, and their ends shall be referred to as "distal" meaning the end which goes into the vessel and "proximal" meaning the other end. Thus, "distal direction" or "distally" shall indicate a general direction from the proximal end to the distal end, and "proximal direction" or "proximally" shall refer to an opposite direction.

The atherectomy system comprises:

A flexible guide wire 140 insertable into the vessel.

A flexible catheter 21 slidable over the flexible guide wire, having a coring means in the form of a tubular blade 22 at its distal end, defining a continuous passage 25 around the flexible guide wire for ingesting the cored plaque.

In smaller versions of the system the proximal end of the flexible guide wire is preferably made of a thin walled stainless steel extension tube 17, whereas in larger versions where a simple tube may prove too stiff to conform to the vessel's anatomy, the extension tube can be constructed like the catheters shown in my above mentioned U.S. Pat. No. 4,819,634. The extension tube 17 is attached to an auger-shaped helical wire 170 which is slidably guided over the flexible pilot wire 160. Bio-compatible coatings or lubricants may be disposed on the extension tube or on the flexible pilot wire or between them to ease their relative motion. A helical void is defined between the coils of the wire 170 for containing and holding the plaque.

A nipple 14 is connected to the proximal end of the extension tube 17 through an annular chamber 15 which slidingly seals around the flexible pilot wire.

The flexible guide wire's section which extends distally into the vessel from the flexible catheter, concentrically aligns the flexible catheter within the vessel, and provides a lever arm which angularly aligns the flexible catheter within the vessel (also note FIG. 5).

When the flexible catheter's distal end 23 bears against the vessel's wall, it does so through a relatively large contact area, spreading the contact force and minimizing any trauma to the vessel.

The atherectomy system uses "mechanical energy" to advance and rotate the tubular blade and additional "auxiliary energy", emitted by the distal end portion of the atherectomy system, to soften a boundary layer of the plaque and ease in the coring process. The auxiliary energy can be in the form of, for example, heat, laser or ultrasound energy. Some of the auxiliary energy can be retrieved by a suitable transducer and transmission means and processed to image the obstruction and its surroundings, making the coring process safer and allowing the physician to assess the results of the procedure.

Coring at least some of the plaque is more efficient than pulverizing it. To illustrate this point, when a tubular blade having a wall thickness of 0.25 mm cores an obstruction with an outside diameter of 5 mm and an inside diameter (lumen) of 1 mm the area of the boundary layer that the tubular blade has to pulverize is only a fifth of the obstruction's area and correspondingly one fifth of its volume.

Suction can be applied to the flexible catheter through a port 33 which communicates with a groove 34 defined by a motor's housing 28', which communicates with hole 39, which communicates with a hollow shaft 29, which communicates with the proximal end of the continuous passage 25. Preferably the suction is provided by a positive displacement pump 33', such as a piston pump or a peristaltic pump, which limits the amount of blood removed through the flexible catheter to the volume that is displaced by the pump. When only free flowing blood is present in the continuous passage the negative pressure in the continuous passage is low but when plaque enters the continuous passage the negative pressure automatically rises and pulls the cut plaque proximally. A feedback control 19 can be used to increase/decrease the pumping rate of pump 33', through wiring 24, in response to sensing through a tube 20, that the negative pressure between the pump and the catheter rose/dropped, respectively, above or below a certain level. The suction can be stopped altogether when the coring is stopped. This further reduces the amount of blood removed from the patient during the procedure. The maximum level of negative pressure can be limited to prevent collapsing of the vessel wall. Coupling means in the form of a conical seat 27 couples it to a drive means in the form of a motor 28 having the hollow shaft 29 with a matching tapered end 31 and a seal 32 at its other end. The hollow shaft and seal are slidingly disposed around the flexible guide wire. A pod 161 is used to emit auxiliary energy, which is sent by the base unit 162 through the flexible pilot wire, to the surrounding tissue, to soften the surrounding plaque, and to optionally retrieve signals in the form of returned auxiliary energy which is sent back to the base unit to be processed to form an image of the obstruction site. Laser energy can be used to obtain a topographical image and ultrasound energy to obtain a geological image. Relying on this information the physician can advance the pilot wire with a reduced risk of perforating the vessel's wall.

The helical wire 170 takes up the free play between the flexible pilot wire 160 and the flexible catheter 21 thereby concentrically aligning one with the other. A void defined between the helical wire's coils serves to hold the plaque during the atherectomy and to restrain the cored plaque from freely rotating around the flexible guide-wire, and to the extent that the plaque is rotated by the flexible catheter this rotation is translated by the helical wire to urge the cored plaque proximally in the continuous passage. The helical wire can be inserted into a tight obstruction by rotating it and threading it into the obstruction. In the process of threading, the helical wire pulls itself across the obstruction and anchors itself in the plaque. When the flexible catheter is pushed forward in the vessel, the flexible guide wire can be pulled to offset the longitudinal force in the atherectomy system. which tends to buckle the flexible catheter, This allows a physician to work around sharp bends in the arterial system such as, for example, when inserting the system into a right leg through the left side of the groin without having the system buckle when the flexible catheter is pushed distally during the atherectomy procedure.

A flexible sleeve 71 in which the flexible catheter is disposed isolates the vessel's wall from the flexible catheter, and can be used to introduce the flexible catheter into the vessel and direct it to the obstruction's site. A nipple 72 is connected to the flexible sleeve through an annular chamber 73 7hich is equipped with a seal 74 which seals around the flexible catheter. The flexible sleeve 71 defines a fluid passageway between the nipple 72 and the atherectomy site for fluid which preferably contains one or more restenosis inhibiting drugs such as, for example; Hirudin, Low-molecular weight heparin, Glucocorticoids, Angiopeptin, Angiotensin, Anti-mitogenics, Antiplatelets antibodies, Endotillin neutralizer. It can be appreciated that there is on-going research in this area which periodically suggests additional drugs that fit this category, which can be delivered by this system, and also the exclusion of drugs that are found to be ineffective inhibitors of restenosis.

FIG. 3 shows a second embodiment of a pod 163 having protrusions 164 on its distal end and a mid section 165 for emitting/receiving auxiliary energy and thereby developing an image of the atherectomy site. The protrusions enable a physician to use the pod to drill and cross hard obstructions by rotating the pilot wire, while the real time image of the atherectomy site provides a margin of safety. The protrusions may range in size from discrete teeth as shown in FIG. 3 and 4 to microscopic protrusions which may be formed by bonding diamond particles to the pod's distal end. Auxiliary energy could be used to assist the pod in penetrating through the obstruction, with or without rotation thereof. The auxiliary energy which is emitted by the pod is transmitted to the adjacent plaque which also eases in threading the helical wire through the obstruction.

Figure 20:
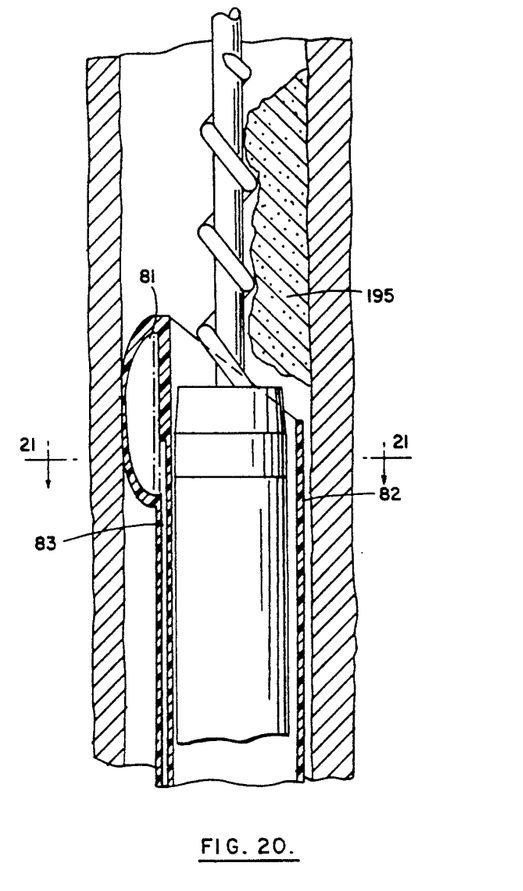
FIG. 20 shows a partially cross sectioned view of an inflatable chamber located at the distal end of the flexible sleeve.
Figure 21:
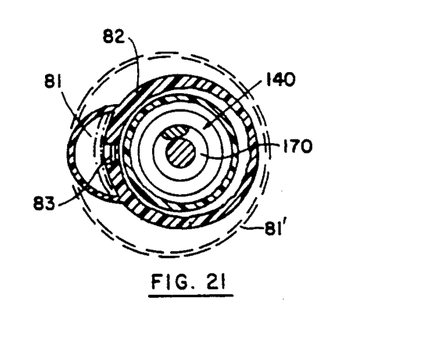
FIG. 21 shows a cross sectioned view of the system shown in FIG. 20, along a line 21—21 marked on FIG. 20.

FIG. 4 shows a distal portion of a flexible pilot wire 160 disposed in a deflecting sleeve 82' having an inflatable chamber 81', for deflecting the trajectory of the flexible pilot wire in the vessel. The deflecting sleeve 82' and inflatable chamber 81' is a scaled down version of a deflecting sleeve 82 and an inflatable chamber 81 that are shown in FIGS. 20 and 21 and performs in the same manner. The deflecting sleeve can be sized to guide the pilot wire or to guide the whole flexible guide wire through the vessel. Fluid containing one or more restenosis inhibiting drugs can be delivered through the sleeve 82' to the atherectomy site.

FIG. 5 shows the trajectory of an atherectomy system in a cross sectioned, curved obstructed vessel, when the coring process is done over a hollow flexible pilot wire 14 and a casing made of a helical wire 170 attached by a weldment 49 to an extension tube 17. An optional inflatable chamber 15 is attached to the pilot wire and can be inflated or deflated through the hollow flexible pilot wire 14 which communicates fluid from its proximal end to an orifice 68. The inflatable chamber can enhance the system's performance by, for example, centering the flexible pilot wire in the vessel, cushioning the contact between the flexible pilot wire and vessel's wall as well as for anchoring it to the vessel's wall. If an asymmetric inflatable chamber is used it can selectively bias the position of the flexible pilot wire in the vessel by rotating the pilot wire to a desired orientation.

FIG. 5' shows two optional blade configurations 22' and 22" that will be discussed later on.

FIG. 6 shows the range of possible trajectories of the system in a cross sectioned, curved obstructed vessel, when the coring process is done over a standard flexible guide wire 35 without the benefit of guidance provided by a casing.

Figures 7, 8:
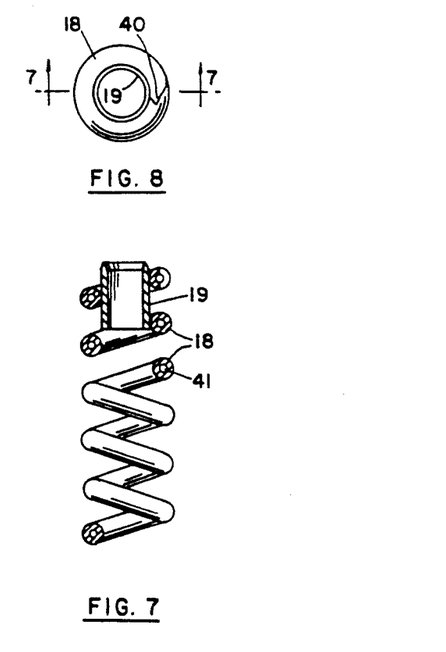
FIG. 7 shows an enlarged, partially sectioned view of the distal end section of a helical wire where the distal entry to the void defined between the coils is partially closed by a short tube.
FIG. 8 shows end view of the helical wire shown in FIG. 7.

FIG. 7 shows an enlarged, partially sectioned view of the distal end section of a casing in the form of a helical wire 18 where the distal entry to the void defined between the coils is partially closed by a thin gate in the form of a short tube 19, preferably made from radio opaque material (for example an alloy comprising gold and/or platinum), attached to the internal diameter of the casing. The helical wire is made of a tube with a lumen 41 that can be used to deliver and emit auxiliary energy through its distal end, making it easier to thread it into the plaque.

FIG. 8 shows an end view of the casing shown in FIG. 7 in the form of a helical wire 18 having a pointed distal end 40 to ease penetration into the plaque.

Figure 9:
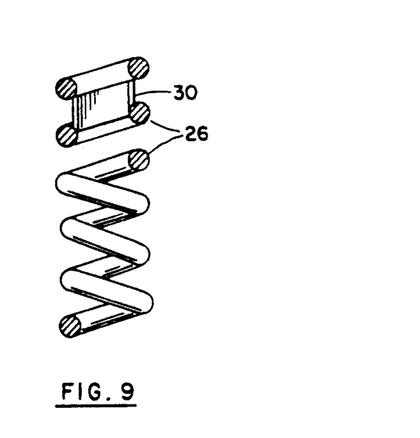
FIG. 9 shows an enlarged, partially sectioned view of the distal end section of a helical wire where the distal entry to the helical void defined between the coils is partially closed by a tube section.

FIG. 9 shows an enlarged, partially sectioned view of the distal end section of a casing in the form of a helical wire 26 where the distal entry to the void defined between the coils is partially closed by a thin gate in the form of a tube section 30, preferably made from radio opaque material and attached between the coils of the helical wire, adjacent to the internal diameter of the casing.

Figure 10:
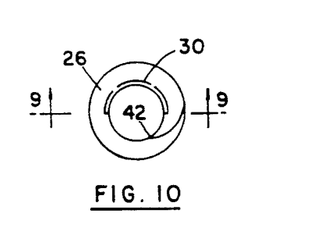
FIG. 10 shows an end view of the helical wire shown in FIG. 9.

FIG. 10 shows an end view of the casing shown in FIG. 9 in the form of a helical wire 26 having a pointed distal end 42, making it easier to thread it into the plaque. As the helical wire 26 is rotated and advanced around a flexible pilot wire the point 42 remains adjacent to the flexible pilot wire. If the flexible pilot wire is disposed against the arterial wall, as the helical wire is advanced and rotated, its inclined leading edge gently separates the arterial wall from the flexible pilot wire and centers it in the vessel. Optionally the pointed distal end can be moved away from the flexible pilot wire, as shown in FIG. 8 and marked by numeral 40, which makes the helical wire thread more aggressively through the plaque while reducing its ability to separate the arterial wall from the flexible pilot wire as discussed above.

Figure 11:
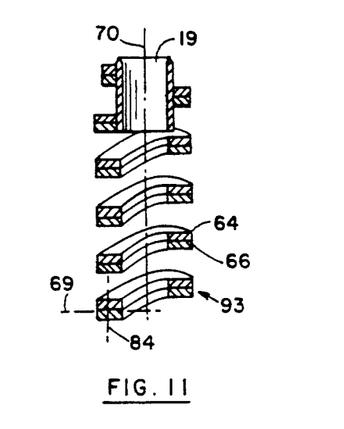
FIG. 11 shows an enlarged, sectioned view of the distal end section of a helical wire made of two flat layers, where the distal entry to the helical void defined between the coils is partially closed by a short tube.

FIG. 11 shows an enlarged, sectioned view of the distal end section of a casing in the form of a helical wire 93 made of two flat layers 64 and 66, where the distal entry to the void defined between the coils is partially closed by a thin gate in the form of a short tube 19 attached to the internal diameter of the casing. The multi layer construction decreases the cross section modulus of the helical wire around a neutral axis 69 which is perpendicular to the main axis 70 of the helical wire 93, as compared with a non-layered construction, but it has minimal effect on the cross section modulus around a neutral axis 84 which is parallel to the main axis 70. This allows the helical wire to flexibly conform to the vessel's anatomy with a minimal loss in its torque carrying capacity which is needed for threading it through the plaque.

Figure 12:
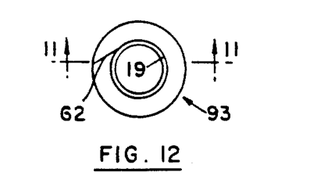
FIG. 12 shows and end view of the helical wire shown in FIG. 11.

FIG. 12 shows an end view of the casing shown in FIG. 11 in the form of a helical wire having a pointed distal end 62 for the purposes discussed above in conjunction with FIG. 10.

Figure 13:
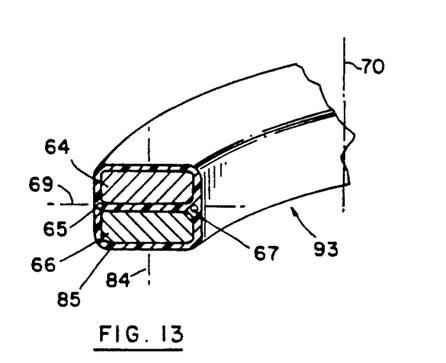
FIG. 13 shows a further enlargement of the cross section of the helical wire of FIG. 12.

FIG. 13 shows a further enlargement of the cross section of the helical wire of FIG. 12. The layers 64 and 66 are encapsulated in plastic 85 which holds them together and makes them thread through the plaque as one piece but is sufficiently flexible to allow their cross section modulus to be close to that of two separate layers. Auxiliary energy conduits 65 and 67, are also encapsulated by the plastic along side the layers of the wire. Preferably, the plastic has a slippery outer surface, making it easier to insert it into the vessel and to thread it into the plaque.

Figure 14:
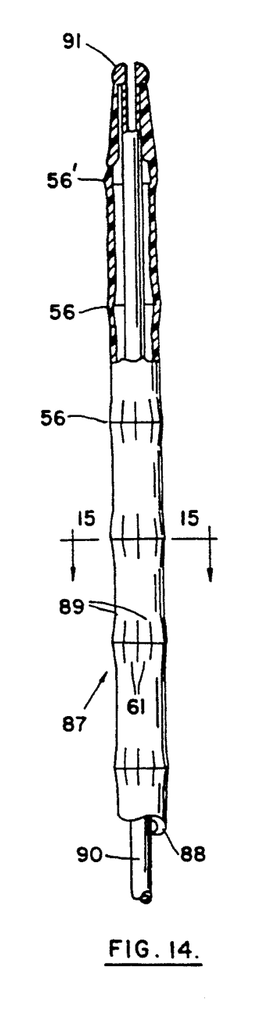
FIG. 14 shows the flexible guide wire used in the embodiment of FIG. 16 with barrier means in their contracted position.
Figure 16:
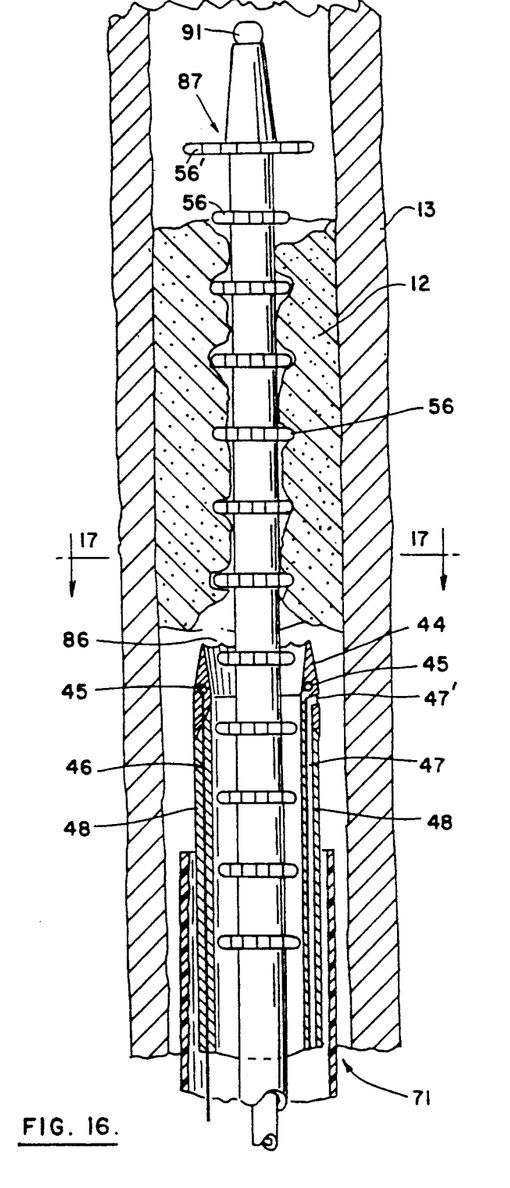
FIG. 16 shows a cross sectioned view of the distal end portion of an atherectomy system with a coring means in the form of a tubular-blade utilizing auxiliary energy, disposed over a flexible guide wire having barrier means in their expanded position.
Figure 17:
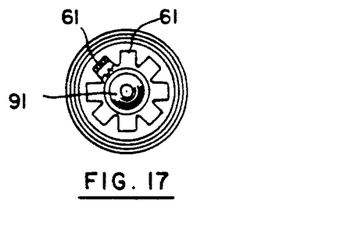
FIG. 17 shows a cross sectioned view of the system shown in FIG. 16 along a line 17—17 marked on FIG. 16.

FIG. 14 shows a flexible guide wire 87 having a hollow pilot wire 90 and a casing in the form of a jacket 88 with arrays of slits 89 which define collapsible and expandable ribs 61. The jacket is slidable over the flexible pilot wire 90, up to an enlarged rounded distal end 91. Under the compressive force which is generated by pushing the proximal end of the jacket while pulling the proximal end of the flexible pilot wire, the ribs fold and expand to form barriers 56, as shown in FIGS. 16 and 17, and at this position they define a void (in this embodiment the term "void" means the gaps defined between barriers 56, collectively. In the previous embodiments it referred to the single continuous helical gap defined between the coils of the helical wire) which holds plaque surrounding it and counters its distal movement during the atherectomy. The diameter of the expanded top barrier element 56' can be made larger than the inner diameter of the flexible catheter to block a larger cross sectional area of the vessel, whereas the other barrier elements are made to fit inside the flexible catheter which they slidably support.

The hollow pilot wire 90 can be used as a conduit for delivering fluids to the obstruction site and beyond, such as; restenosis inhibiting drugs, radio opaque fluid to assist in fluoroscopic imaging of the vessel, oxygen rich fluid for providing nourishment to deprived cells during the procedure, or fluid for irrigating the work site. Additionally the hollow pilot wire can be used to deliver restenosis inhibiting drugs to the obstruction site and beyond.

Figure 15:
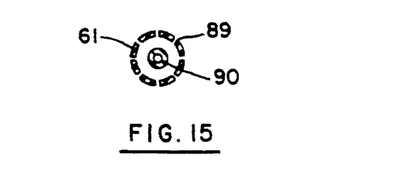
FIG. 15 shows a cross sectioned view of the flexible guide wire shown in FIG. 14 along a line 15—15 marked on FIG. 14.

FIG. 15 shows a cross sectioned view of the flexible guide wire shown in FIG. 14.

FIG. 16 shows a distal end portion of an atherectomy system having a coring means in the form of a tubular blade 44. A conduit 47 located in the wall of a flexible catheter 48 carries fluids, for example, restenosis inhibiting drugs, and emits the fluids through an orifices 47' to the atherectomy site.

The blade has a ring shaped element 45 which receives auxiliary energy by means of at least one conduit 46, also located in a wall of the flexible catheter, and this energy is emitted to the surrounding plaque. The emitted energy may have several forms which assist the blade in coring the plaque. If the auxiliary energy is thermal the ring can be a resistive element to which the conduit carries electrical current, or, the ring can be made to absorb and distribute laser energy and then the conduits would be made of optical fibers. Optionally, the tubular blade can be made from semi-transparent or transparent material in order to transmit part or all of the laser energy directly to the plaque. If the emitted energy is ultrasound energy the ring can comprise a piezoelectric transducer to which the conduits carry electrical current.

The auxiliary energy that is delivered to the tubular blade eases the coring process by softening the boundary layer, and since the plaque is positively held in the void defined by the flexible guide wire 87 it may be possible to core the plaque by simply pushing the catheter, especially where there is an anatomical reason not to impart torque onto the vessel by the rotation of the catheter; for example, when working in a recently implanted arterial graft that is poorly attached to the surrounding tissue. However, rotating the catheter is preferable because the cutting and coring is more effective and because it minimizes the frictional resistance to the advancement of the flexible catheter into the vessel (a relative motion of two surfaces in one direction minimizes the frictional resistance to their relative motion in a perpendicular direction). For the same reason the relative rotation between the flexible catheter and the plaque eases the proximal movement of the plaque in the flexible catheter.

The tubular blade is shown equipped with serrated teeth 86. Alternatively the cutting edge can be made with straight teeth or can be made with a smooth edge as shown the embodiment of FIG. 2.

FIG. 17 shows a partially cross sectioned view of the system shown in FIG. 16.

Figure 18:
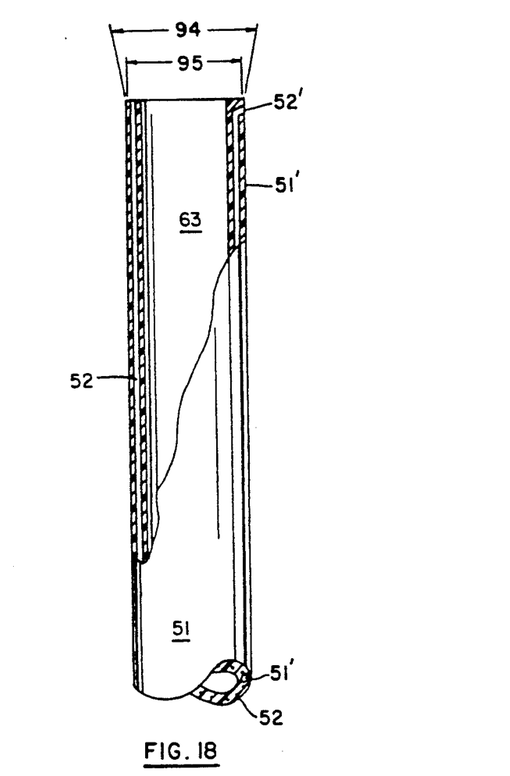
FIG. 18 shows a cross sectioned view of an atherectomy system where the coring means utilizes a radiation emitting device (the flexible guide wire is omitted).

FIG. 18 shows a flexible catheter 51 with a coring means utilizing auxiliary energy, preferably in the form of laser energy carried by optical fibers 52, which is emitted through their distal ends. The auxiliary energy cores the obstruction by ablating a narrow boundary layer in it and the continuous passage 63 ingests the cored plaque as in previous embodiments. Similarly to the tubular-blade, the laser based coring means is efficient and uses less energy in comparison to other laser based systems which ablate all the plaque of the obstruction.

Optionally, the emitted laser energy can be directed in a slightly /utwardly inclined direction as shown in FIG. 18, so that a wider boundary layer of plaque would be ablated to make the diameter 94 of the recanalized vessel larger than the diameter 95 of the flexible catheter 51 and larger than the puncture would that is needed to introduce the flexible catheter into the vessel, while the center part of the obstruction can still be cored unpulverized.

A conduit 51' is located in the wall of the flexible catheter and leads to an orifice 52' for delivering fluids, preferably restenosis inhibiting drugs, to the atherectomy site.

The flexible catheter 51 can be disposed in any of the sleeves shown in connection to the embodiments of the present invention. By using a sleeve equipped with a toroidal chamber to block blood flow as explained above and by introducing fluid to the obstruction site, for example saline solution, through the sleeve or the flexible catheter, a working medium of choice can be created to suite a specific type of radiation and to allow visual or spectroscopic analysis of the vessel's lumen.

As previously discussed, the auxiliary energy may enable the physician to core the plaque by pushing the flexible catheter with or without rotating it.

Figure 19:
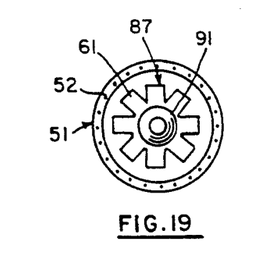
FIG. 19 shows a distal end view of the system shown in FIG. 18.

FIG. 19 shows an end view of the atherectomy system shown in FIG. 18.

FIGS. 20 and 21 show a biasing means in the form of an asymmetrical inflatable chamber 81 formed at the distal end of a flexible deflecting sleeve 82 which, when inflated, through a channel 83 formed in the sleeve's wall, bears against the vessel's wall, as shown in solid lines, eccentrically biasing the flexible sleeve and the coring means towards an eccentric obstruction 195. When deflated, as shown by phantom lines, the chamber conforms to the sleeve to minimize interference with its insertion into the vessel. Alternatively the chamber can be shaped as an asymmetrical toroidal inflatable chamber 81' as shown in FIG. 21 by interrupted lines. This chamber, when inflated, establishes peripheral contact with the vessel's wall and thereby blocks blood flow between the sleeve and the vessel's wall, as well as eccentrically biasing the sleeve (it can be understood that a symmetrical toroidal chamber can be provided for the purpose of blocking the flow around the sleeve while centering the biasing sleeve). Any of the above mentioned chambers can also be inserted into the lumen that has been cored by the coring means, to be inflated therein with sufficient pressure, and to further widen the lumen, however, such a procedure may introduce some of the drawbacks of angioplasty.

Figure 22:
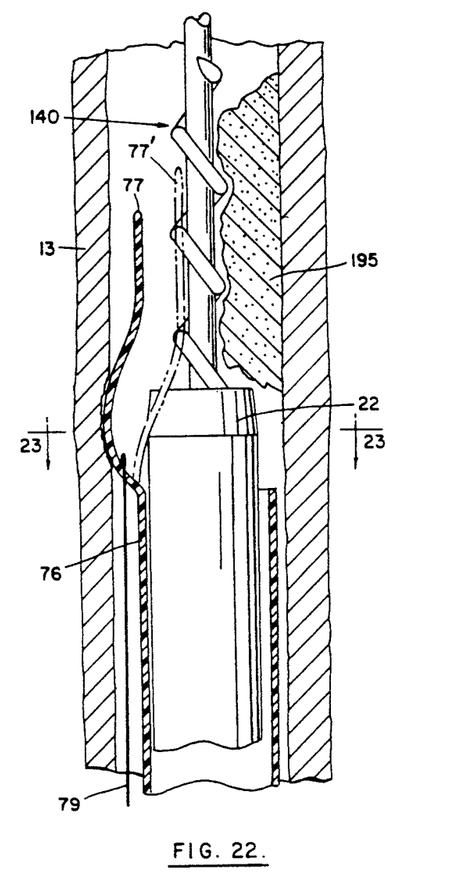
FIG. 22 shows a partially cross sectioned view of an atherectomy system with a flexible sleeve having a selectively actuatable tongue at its distal end.
Figure 23:
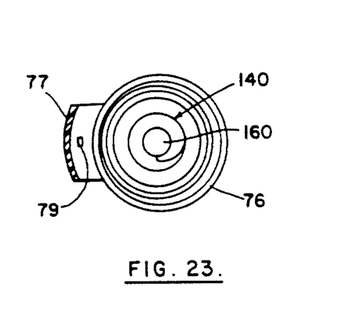
FIG. 23 shows a partially cross sectioned view of the system shown in FIG. 22 along the line 23—23 marked on FIG. 22.

FIGS. 22 and 23 show an atherectomy system where a flexible sleeve 76 has a tongue 77 which can be used when coring an eccentric obstruction 195. In such a case the tongue can be inserted opposite of the obstruction to protect the vessel wall and bias the trajectory of the coring means into the obstruction. The tongue can be energized against the vessel's wall by tensioning a flexible rope 79, moving the tongue from its relaxed position which is shown by a phantom line in FIG. 22 and marked 77' to the position shown in solid lines and marked 77.

OPERATION

FIG. 5 shows a first a portion of the flexible pilot wire 14, inserted in a curved vessel. Then a casing in the form of the helical wire 170 is inserted over the flexible pilot wire, preferably by threading it through the obstruction. The flexible pilot wire acts as a lever arm 3 to angularly align and safely guide the advancing helical wire 170 through the curved vessel. Without the lever arm's guidance the advancing helical wire would contact the vessel's wall at approximately a point 1 and exert a large concentrated compressive force (which would possibly injure the arterial wall) until the bending moment which equals the product of that force multiplied by the short lever arm 2 would be sufficient to bend the helical wire around an axis 5 perpendicular to the plane of curvature of the vessel (and therefore shown perpendicular to the drawing sheet by a checkered circle). In comparison, with the flexible pilot wire's longer lever arm 3 the required force is smaller and it is spread by the lever arm over a longer and larger contact area of the vessel's wall.

Once the helical wire is in place it reinforces and holds the plaque preparatory to coring. At this point the physician has an opportunity to, fluoroscopically or by the use of auxiliary energy imaging, assess the position of the flexible guide wire in the vessel. The distal portion of the flexible guide wire serves to concentrically align the advancing flexible catheter within the vessel and also serves as a lever arm which angularly aligns the flexible catheter within the vessel during the atherectomy. The angular alignment of the flexible catheter by the flexible guide wire is very similar to the alignment of the helical wire over the flexible pilot wire; the flexible catheter is inserted over the flexible guide wire which acts as a lever arm 4 to angularly align and safely guide the advancing flexible catheter 48. Without the lever arm's guidance the advancing coring means would contact the vessel's wall at approximately the point 1 and exert a large concentrated compressive force until the bending moment which equals the product of that force multiplied by the short lever arm 2 would be sufficient to bend the flexible catheter around the axis 5, however such a compressive force will likely cause the coring means to injure the vessel's wall. In comparison, with the flexible guide wire's longer lever arm the required force is smaller and it is spread by the lever arm over a longer and larger area of the vessel's wall. Thus, it can be seen that by aligning the system with the vessel, concentrically and angularly, the atherectomy system extracts the plaque while minimizing injury to the vessel's wall and thereby minimizing any hyperplasia that is triggered by such injury.

To further minimize restenosis, the flexible catheter 48 is adapted to deliver restenosis inhibiting drug to the atherectomy site. The drug delivery system (which is shown on a larger scale in FIG. 16) comprises conduit 47 and port 47'. As the flexible catheter advances and rotates along the phantom lines marked on FIG. 5 it delivers fluid containing at least one restenosis inhibiting drug directly to the lumen that is being created by the atherectomy process (neolumen). Due to the intimate contact between the coring means and the neolumen the drug is directed in high concentrations into the neolumen's wall and the mechanical rubbing of the coring means against the neolumen enhances the drug's delivery to the neolumen's surface.

FIG. 5' shows two optional blade configurations. The right hand configuration shows a blade 21' where the sharp edge is formed on the internal diameter of the blade and is connected by a taper to the external diameter. The taper acts to distance the sharp edge from the arterial wall making it a safer configuration preferred for working in a torturous vessel. If the blade is smooth the taper does not pulverize the boundary layer but tends to displace it outwardly.

The left hand configuration shows a blade where 22" the sharp edge is formed on the external diameter and is connected by an inverted taper to the internal diameter. If the blade is smooth the inverted taper does not pulverize the boundary layer but tends to displace it inwardly and core it, however, with this configuration there is a higher probability of injuring the arterial wall. A design compromise between these two configurations is shown in FIGS. 5, 6 and 16, where the sharp edge is formed between the internal and external diameters.

FIG. 6 illustrates the potential risk of injuring the vessel's wall 7hen the coring process is done over a standard flexible guide wire without a casing. As the tubular blade advances along the flexible guide-wire its trajectory can vary, angularly and eccentrically, in the range defined between the two phantom lines, and segments of the vessel's wall may be injured, causing undesirable short term damage and long term damage (restenosis).

Generally, the process of removing plaque from within a patient's vessel with an atherectomy system, and applying at least one drug to the atherectomy site, comprises the following steps:

Inserting into a vessel, into an obstruction, a flexible guide wire to preferably engage and hold the plaque in place.

Advancing over the flexible guide wire a blade located at a distal end of a flexible catheter and forming in the vessel a neolumen.

Applying at least one restenosis inhibiting drug to the neolumen.

The sequence of inserting the system's components into the vessel may be varied. Steps may be combined to streamline the process or steps may be added to improve the process. The process may be customized according to the characteristics of the individual obstruction and its location. For example; the system may be introduced percutaneously (that is through the skin), or intra-operatively (that is when the vessel is surgically exposed for accessing it), a standard guiding catheter (straight or pre-formed) may be used as a sleeve and inserted into the vessel to assist in positioning the system's components in the obstruction site.

The preferred mode of operating an atherectomy system, having an auger-shaped flexible guide wire, is to first thread the flexible guide wire by rotating it in one direction crossing the obstruction like with a corkscrew, and then advance and rotate the flexible catheter in an opposite direction while the flexible guide wire is stationary. However, to increase the auger's ability to proximally convey material it is possible to rotate the flexible guide wire and to apply suction to the proximal end of the flexible catheter, especially when coring an obstruction with a slurry-like consistency such as fresh blood clots.

An atherectomy system can be manufactured in different diameters and lengths depending on the size and site of vessel that it is intended for and on whether the system is to be used percutaneously or intra-operatively.

It can be noted from the FIGURES that the basic components of the atherectomy system can have several optional features and design variations. The flexible catheter can be made from plastic or metal or from a combination thereof and the coring means can utilize mechanical energy and/or auxiliary energy. The flexible guide wire can be equipped with various types of casing designs, some of which are affixed to the pilot wire and others that are slidable thereon. The sleeve can be equipped with mechanical or hydraulic biasing means. By combining a flexible catheter with certain features, a flexible guide wire with certain features, and a sleeve with certain added features a variety of customized atherectomy systems can be made. This increases the user's ability to match the system's characteristics with the specific disease condition that is being treated, which is helpful, since the clinical characteristics of arterial atherosclerotic obstructions vary in their topography, geology and accessibility from one patient to another.

The above and other modifications and substitutions can be made in the system and in its operation without departing from the spirit of the invention or the scope of the following claims.

I claim:

1. A process for inserting into a vessel a flexible guide wire, comprising the following steps;
    a) suspending a body part, containing the vessel, in a de-compression chamber,
    b) lowering the pressure in the de-compression chamber sufficiently, to dilate the vessel, and
    c) inserting the flexible guide wire into the dilated vessel.

* * * * *